United States Patent
Appling et al.

(10) Patent No.: US 9,314,561 B2
(45) Date of Patent: Apr. 19, 2016

(54) FILTER AND FRAME APPARATUS AND METHOD OF USE

(71) Applicant: Delcath Systems, Inc., New York, NY (US)

(72) Inventors: William M. Appling, Granville, NY (US); Stephen N. Engelhard, Queensbury, NY (US); Matthew G. Barton, Wilton, NY (US)

(73) Assignee: Delcath Systems, Inc., New York, NY (US)

( * ) Notice: Subject to any disclaimer, the term of this patent is extended or adjusted under 35 U.S.C. 154(b) by 404 days.

(21) Appl. No.: 13/731,016

(22) Filed: Dec. 30, 2012

(65) Prior Publication Data

US 2013/0168303 A1    Jul. 4, 2013

Related U.S. Application Data

(60) Provisional application No. 61/581,496, filed on Dec. 29, 2011.

(51) Int. Cl.

| | |
|---|---|
| *A61M 1/36* | (2006.01) |
| *B01D 24/00* | (2006.01) |
| *B01D 25/00* | (2006.01) |
| *B01D 29/52* | (2006.01) |
| *B01D 35/30* | (2006.01) |

(52) U.S. Cl.
CPC ........... *A61M 1/3626* (2013.01); *A61M 1/3639* (2013.01); *A61M 1/3679* (2013.01); *B01D 25/002* (2013.01); *B01D 35/306* (2013.01); *B01D 24/002* (2013.01); *B01D 25/06* (2013.01); *B01D 29/52* (2013.01); *Y10T 29/49826* (2015.01)

(58) Field of Classification Search
None
See application file for complete search history.

(56) References Cited

U.S. PATENT DOCUMENTS

| | | | |
|---|---|---|---|
| 4,062,773 A | 12/1977 | Leonard | |
| 4,068,521 A * | 1/1978 | Cosentino | A61B 8/481 600/437 |
| 5,114,570 A * | 5/1992 | Nelson et al. | 210/94 |
| 5,296,137 A * | 3/1994 | Gershon et al. | 210/253 |
| 6,117,100 A | 9/2000 | Powers et al. | |
| 6,315,895 B1 | 11/2001 | Summerton et al. | |
| D656,578 S | 3/2012 | Sherman et al. | |
| D656,579 S | 3/2012 | Sherman et al. | |
| 2003/0234221 A1 | 12/2003 | Johnson et al. | |
| 2005/0118059 A1 | 6/2005 | Olsen et al. | |
| 2010/0012588 A1 | 1/2010 | Siewinski et al. | |
| 2011/0033704 A1 | 2/2011 | Nakao et al. | |
| 2011/0120930 A1 | 5/2011 | Mishkin | |
| 2012/0006751 A1 * | 1/2012 | Ramaswamy et al. | 210/660 |

OTHER PUBLICATIONS

International Search Report and Written Opinion for International application No. PCT/US2012/072225.

* cited by examiner

*Primary Examiner* — Benjamin Kurtz
(74) *Attorney, Agent, or Firm* — Morgan Lewis & Bockius

(57) ABSTRACT

Provided is a filter apparatus, comprising two or more filter cartridges having a first end with an inlet and screen and a second end with an outlet and screen, and walls to contain a filter media held in a housing for holding the two or more filter cartridges in about the same orientation, and an attachment clamp connected to the housing. Also provided is a housing for holding two or more filter cartridges in about the same orientation and a method of using the filter apparatus and housing.

21 Claims, 10 Drawing Sheets

FILTER AND FRAME APPARATUS AND METHOD OF USE

CROSS-REFERENCE TO RELATED APPLICATIONS

This application claims priority benefit of U.S. Provisional Patent Application Ser. No. 61/581,496 filed Dec. 29, 2011, and entitled "Dual Filter Cartridge and Frame Apparatus and Method of Use." The disclosure of the aforementioned Provisional Patent Application Ser. No. 61/581,496 is hereby incorporated by reference in its entirety.

BACKGROUND

Filtering toxic compounds from blood has been an area of great importance for human health. Filters for adsorption of toxic compounds from blood are known in the art. An example is the use of extracorporeal filters to remove chemotherapeutic drugs from the blood stream during cancer treatments such as in hepatic chemosaturation therapy. This therapy also known as percutaneous hepatic perfusion (PHP) delivers ultra-high doses of intra-arterial chemotherapy directly into the isolated liver, saturating both the liver and the tumor cells. The blood from the liver is drained through an isolation-aspiration catheter, and then directed outside the body to specially designed, and often proprietary, filters which reduce the concentration of chemotherapeutic agent before this blood is returned to the body. The potential of chemosaturation therapy includes: the ability to administer higher doses of chemotherapeutic agent to a particular organ than could be delivered with traditional systemic-intravenous methods while significantly reducing systemic exposure to the high dose levels.

The filters used to absorb the drug from the blood are incorporated in an extracorporeal circuit. The blood drained from the liver through the isolation aspiration catheter is pumped by a venous bypass pump, such as is used in heart bypass surgery, through a filter or set of filters. The outlet of the filter(s) is connected by a tube set to a return catheter inserted in a central vein, through which the cleaned blood is returned to the patient's circulatory system. In use, the filter(s) are required to absorb drug at an efficiency which protect the patient's systemic circulation from toxic side effects of high drug concentrations. During use with certain drugs such as Melphalan Hydrochloride, poor filtration can cause side effects such as anemia, thrombocytopenia, neutropenia, together commonly known as Myelo Suppression. Other drugs at high concentrations have risk of cardio toxicities if poor filtration fails to reduce systemic concentrations to safe levels.

Filters, pumps, and connecting tubing are typically set up and assembled by a perfusionist, or other technician, prior to the case. Filters may be clamped or taped to equipment such as IV poles. Multiple filters are often used to aid efficiency. Many times hardware such as lab clamps can become misplaced between cases wasting time to find or forcing the technician to improvise a support method at the last minute.

The system, including filters, is connected to catheters for withdrawal and return of blood to the patient. For the entire system all surfaces exposed to body fluids should be kept sterile.

Prior to use, the filters, blood circuit tube set, and pump are prepared for the procedure. The filters are required to be primed with saline to remove all air from the filter media and to be flushed with saline to remove any fine particulate in the media prior to blood being introduced to the circuit. Proper priming is critical to filter performance. Removing air is necessary to eliminate the potential for air to be infused into the patient. Also, any air left in the filter reduces the surface area that blood will contact the filter media thus reducing filter efficiency.

SUMMARY

The inventors have recognized some problems with prior art filters and provide herein an apparatus that can solve many of the problems in the prior art.

Where multiple filters are used, the set up procedure can become cumbersome and unsteady. Technicians will need to use a variety of hardware to clamp the filters to a support.

If filters were to fall, sterility could be comprised, or catheters could be dislodged from the patient's body. Additionally, filters could crack or leak exposing technical staff and equipment to high concentrations of toxic compounds such as chemotherapeutic drugs.

If the filters are clamped in place to a support or taped together, it may be difficult to see the entire filter's circumference and this will hinder the priming process where air bubbles are to be removed. Additionally, if a technician attempts to turn the filters to visualize the circumference, the mounting method may need to be repeated.

Additionally, during use filters may not see the same resistance to flow if they are angled or set at different heights relative to each other. In accordance with an advantageous feature of some embodiments of the invention, the filters are held in about the same orientation. This will enable about the same flow resistance in each filter such that blood flows about equally through each filter. When filtering drugs from blood it is desirable that each filter provides the same flow resistance so that blood equally flows through each filter. A reduction in flow in one filter may allow thrombus formation in the low flow filter which can continue to develop until flow is completely stopped in that filter. The other filter then provides for the majority, and possibly 100% of the flow and filtration. If the flow rate remains the same, and the total filter volume is decreased or possibly reduced by 50%, the residence time will decrease thus reducing filter efficiency. Additionally, having all flow forced through only one filter may lead to complete saturation of the filter media and limit the filters ability to absorb or filter drug from the blood. Reduced filter efficiency may lead to an increase in adverse reactions caused by the toxic effects of the chemotherapeutic drug not adsorbed by the filter.

The inventors recognized that that these problems could be solved by providing, in some embodiments of the invention, a filter system, apparatus, and method which allows the technician to quickly and securely attach the filter housing to a support without the need for additional hardware. Filter cartridges can be easier to prime and verify all air is removed if the housing allows the cartridges to be rotated so that all areas of the filter can be visualized. The system will guarantee that filters have the same flow conditions if the housing mounts all filter cartridges at the same height and orientation. Combining filter cartridges in a rugged frame housing will increase durability of the product. In some embodiments of the invention, provided herein is a filter system and apparatus wherein the housing of the apparatus enables the filter cartridges to be rotated so that all areas of the filter can be visualized, the housing mounts all of the filter cartridges at the same height and orientation, and the filter cartridges are combined in a rugged frame housing that provides durability. The combination of these features results in an easy to use and robust filter system that protects the equipment and staff from inadvertent breakage. The apparatus allows for the holding of filter cartridges in about the same orientation. The filter cartridges being held in about the same orientation allows for the flow to be about the same in the different cartridges.

In some embodiments, the invention is a filter system where multiple filter cartridges are mounted in a single frame housing. The housing includes a built in clamping mechanism that deploys to allow the filter to be mounted to an IV pole or other suitable and available structure in an operating room. A technician can simply open the sterile supplied filter system, deploy the mounting mechanism, and clamp the assembly to an available IV pole or other supporting member available in the operating room. The housing is mechanically strong and provides a very solid attachment to the support with no risk of falling and no need to improvise a clamping means. The cartridge is allowed to rotate within the housing during priming so that all areas of the filter can be visualized to verify air has been removed. The housing also insures that both filters are mounted in the same orientation and height which guarantees that each filter sees the same flow conditions.

In some embodiments, provided is a filter apparatus, comprising two or more filter cartridges having a first end with an inlet and screen and a second end with an outlet and screen, and walls to contain a filter media, a housing for holding the two or more filter cartridges in about the same orientation, and an attachment clamp connected to the housing. In some embodiments the housing comprises an upper plate and a lower plate for holding the two or more filter cartridges, the upper plate and the lower plate comprising openings for rotatably engaging the two or more filter cartridges, and one or more support elements connecting the upper plate and the lower plate. By providing for the rotation of the filter cartridges, a medical professional can examine the filter media in the where the cartridges are made of a transparent material. Examination of the filter media is often useful in various stages of medical procedures that comprise filtration such as when the filter media needs to be primed for filtration. Priming often comprises removal of trapped gas bubbles in the filter media and being able to notice whether bubbles are trapped in the filter media will help facilitate the priming process.

In some embodiments of the filter apparatus, the attachment clamp is connected to one or more of the one or more support elements. In some embodiments, the one or more support elements comprise a combination of rods and support plates. In some embodiments the attachment clamp is a pole clamp.

In some embodiments of the filter apparatus the walls that contain the filter media comprise a cartridge tube. In some embodiments, the cartridge tube is transparent.

In some embodiments of the filter apparatus the inlet and outlet comprise an inlet connector and an outlet connector. In some embodiments, the outlet connector is connected to the cartridge tube by an outlet flange. In some embodiments, the outlet flange is conical.

In some embodiments, the inlet connector is connected to the cartridge tube by an inlet flange.

In some embodiments of the filter apparatus, the filter media comprises activated carbon. In some embodiments, the filter media is hydrogel coated activated carbon.

In some embodiments of the filter apparatus, the walls to contain the filter media define a cylindrical shape.

In some embodiments, provided is a filter apparatus, comprising two filter cartridges having a first end with an inlet comprising an inlet connector connected to the cartridge tube by an inlet flange and screen and a second end with an outlet comprising an outlet connector and connected to the cartridge by a conical outlet flange and screen, and a transparent cartridge tube to contain a filter media, a housing for holding the two filter cartridges in about the same orientation comprising an upper plate and a lower plate for holding the two filter cartridges, the upper plate and the lower plate comprising openings for rotatably engaging the two filter cartridges, support elements comprising support plates and rods connecting the upper plat to the lower plate, and a pole clamp connected to the support plates.

In some embodiments, the filter apparatus the cartridge tubes of the filter apparatus are comprised of a transparent material selected from a polysulfone, a polycarbonate, a polypropylene, an acrylic, or combinations thereof.

In some embodiments, provided is a housing for holding two or more filter cartridges in about the same orientation, comprising a connected structure comprising an upper plate and a lower plate, the upper plate and the lower plate comprising openings for rotatably engaging the two or more filter cartridges, one or more support elements connecting the upper plate and the lower plate, and an attachment clamp connected to the housing.

In some embodiments, a method is provided for setting up a filter apparatus for a hemo filtration therapy, comprising attaching a filter apparatus according to claim 1 to an IV pole and rotating the cartridges to observe if there are lodged bubbles in the filter media. In some embodiments of the method, the housing is a connected structure.

DETAILED DESCRIPTION

Figure 1:
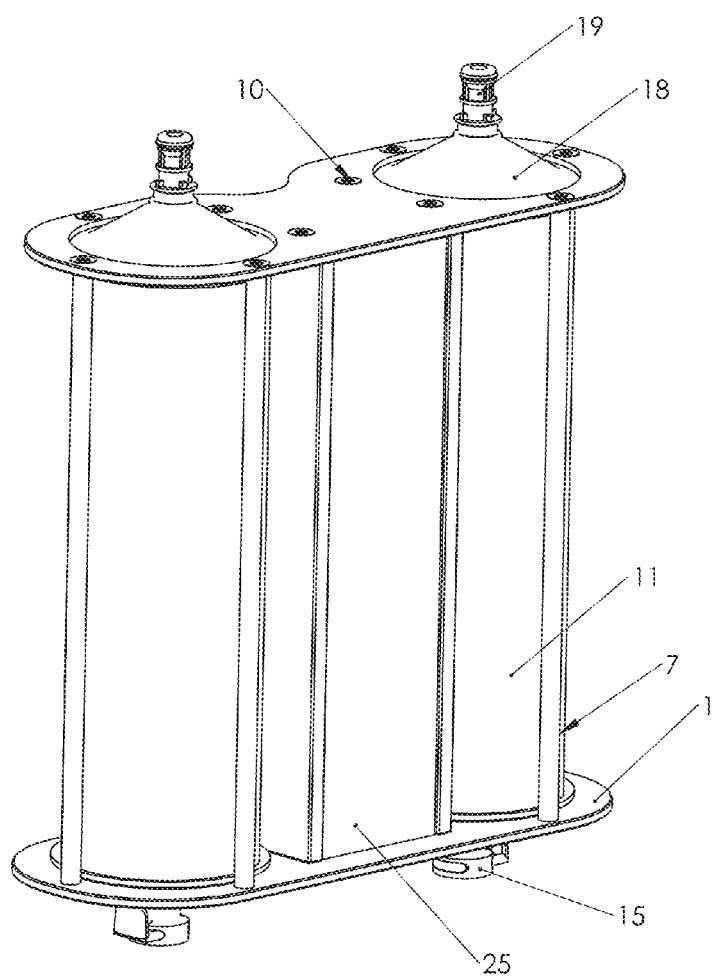
FIG. 1 shows a perspective view from the front of dual filter cartridges mounted in a single frame.
Figure 2:
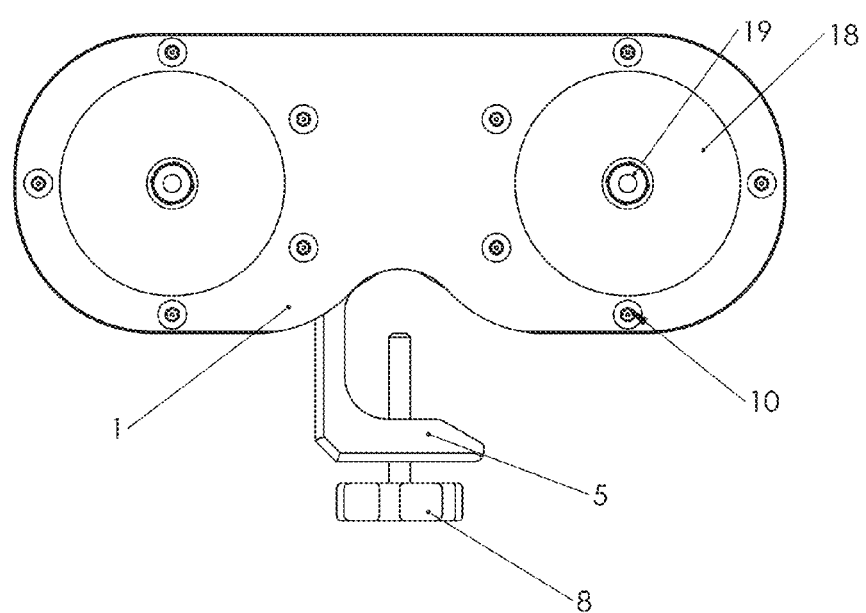
FIG. 2 shows a top view of dual filter cartridges mounted in a single frame with the mounting means deployed for connection.
Figure 3:
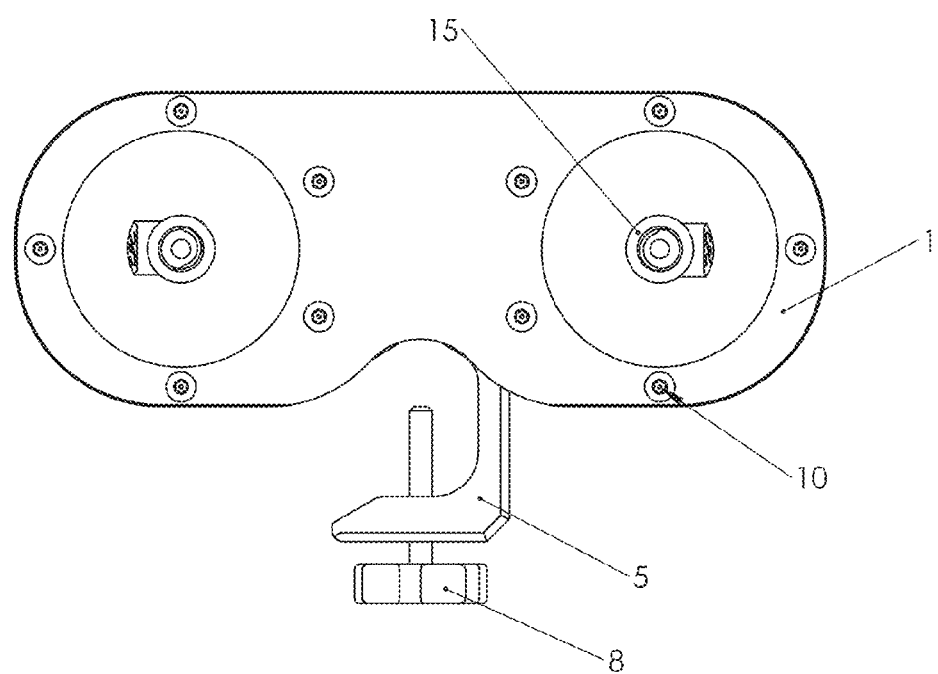
FIG. 3 shows a bottom view of dual filter cartridges mounted in a single frame with the mounting means deployed for connection.
Figure 4:
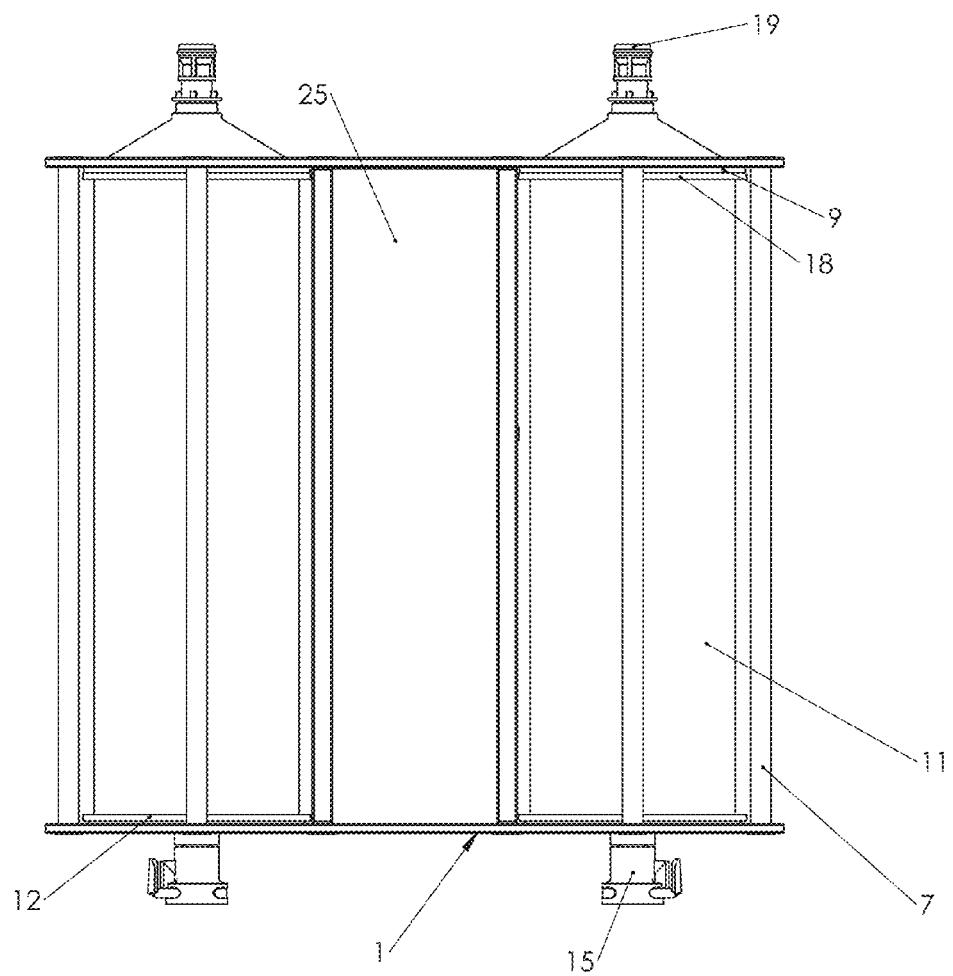
FIG. 4 shows a front view of dual filter cartridges mounted in a single frame.
Figure 5:
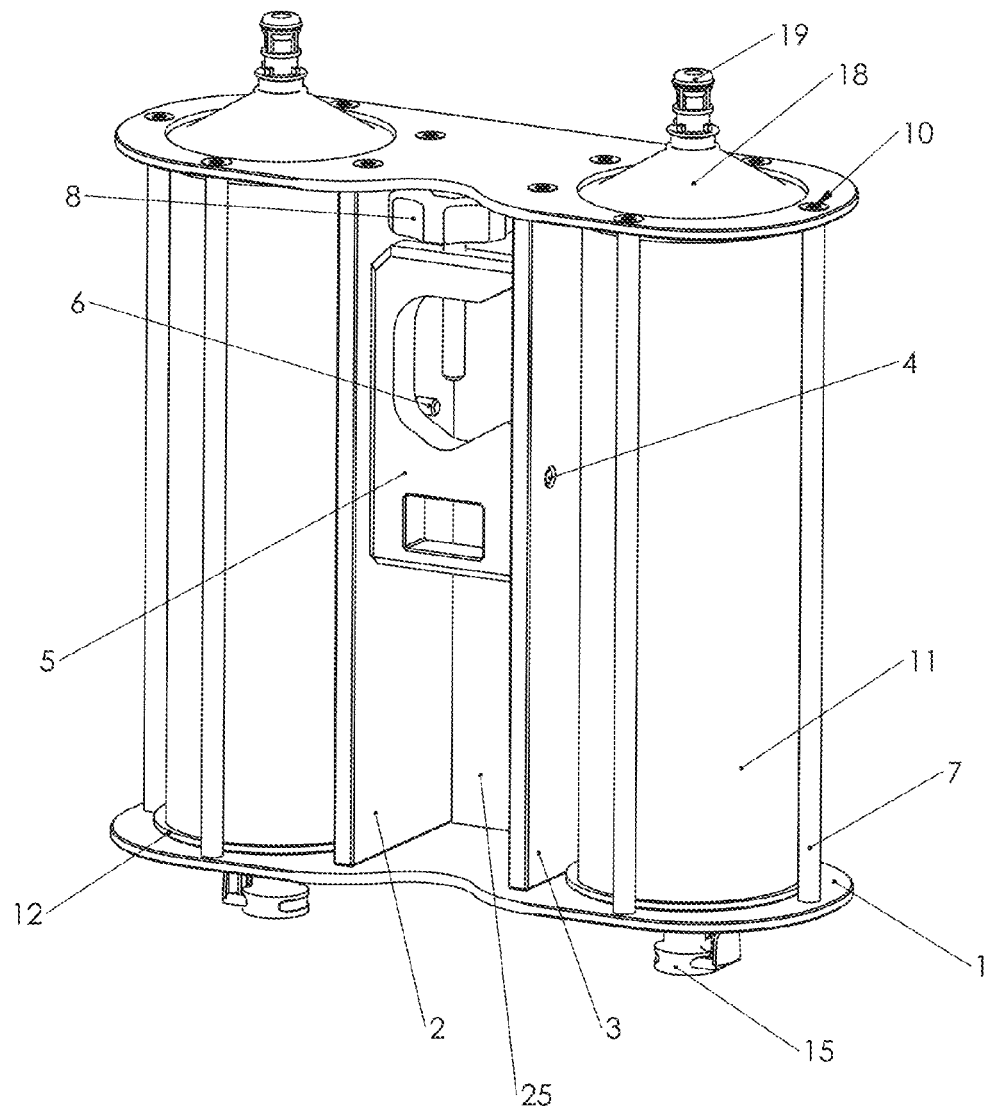
FIG. 5 shows a perspective view from the back of dual filter cartridges mounted in a single frame with mounting means stowed for packaging.
Figure 6:
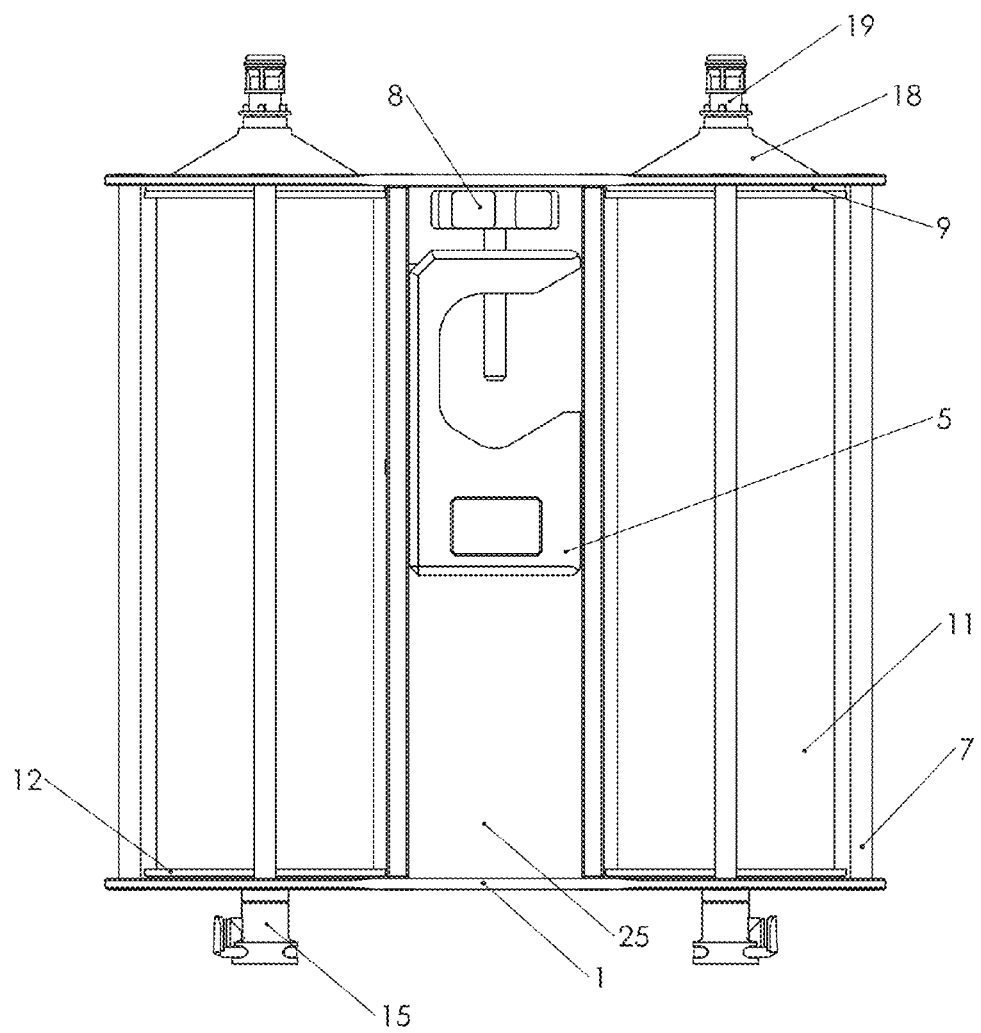
FIG. 6 shows a back view of dual filter cartridges mounted in a single frame with mounting means stowed for packaging.
Figure 7:
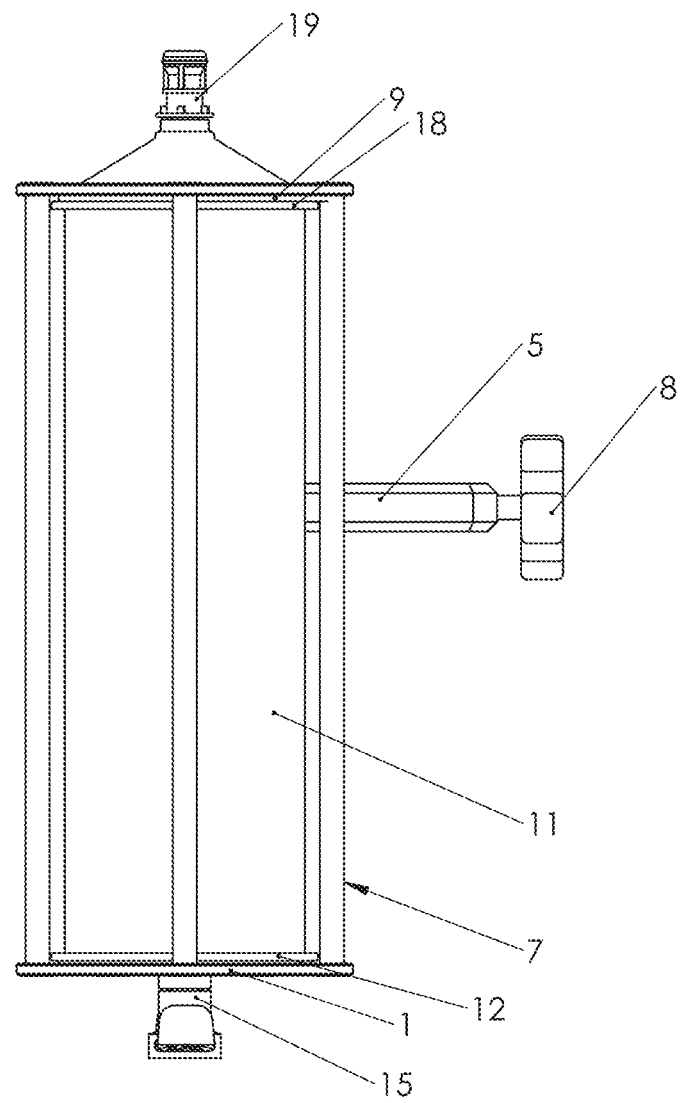
FIG. 7 shows a side view of dual filter cartridges mounted in a single frame with the mounting means deployed for connection.
Figure 8:
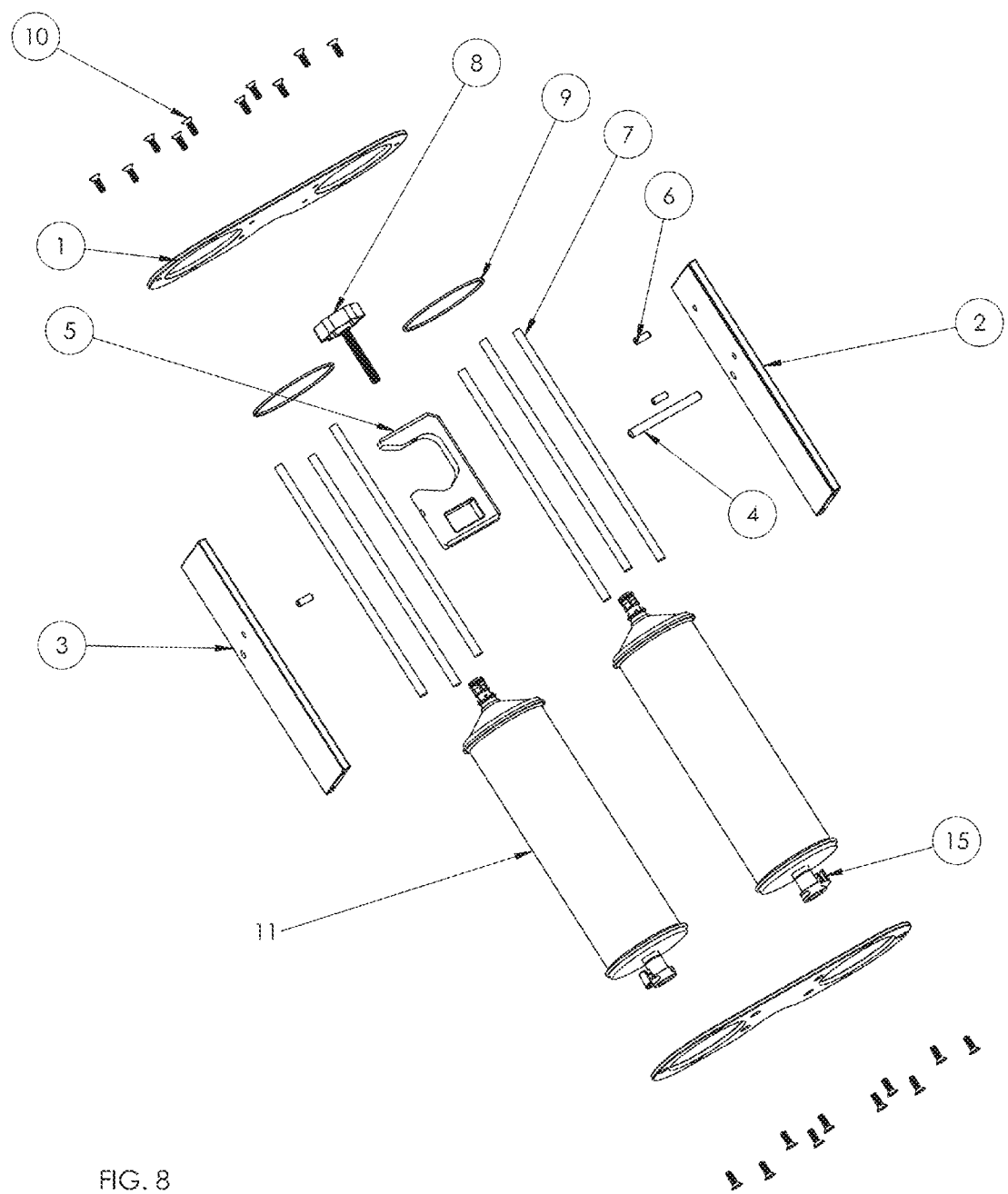
FIG. 8 shows an exploded view of dual filter cartridges and housing.

In some embodiments, a filter cartridge can be made in the following way by assembling lower inlet flange 12 to the cartridge tube 11, to the upper outlet flange 18. An inlet connector 15 is connected to lower inlet flange 12. In some embodiments, an inlet screen (not shown) is incorporated at the inside end of a cartridge tube 11 at the joint between the lower inlet flange 12 and cartridge tube 11. In some embodiments, filter media can be added to the assembly by filling the inside volume of cartridge tube 11. An outlet connector 19 is connected to upper outlet flange 18. An outlet screen (not shown) is incorporated at the inside ends of cartridge tube 11 at the joint between the upper outlet flange 18 and cartridge tube 11. The screens provide a means to keep filter media (not shown), typically small spheres or beads, within the filter cartridge while allowing blood to flow into, through, and out of the filter. The screens can be formed of a suitable polymer with a 200-400 micron mesh. The flanges 12 and 18 and tube 11 can be formed from any suitable transparent plastic such as a polysulfone, a polycarbonate, a polypropylene, an acrylic, and the like. In some embodiments, combinations of these transparent materials can be used. The connections between components can be joints formed by adhesive such as two part epoxy or ultraviolet light curing epoxy, or the joints can be heat welded by means such as radio frequency welding, induction welding, or ultrasonic welding.

The housing is assembled from structural components. In some embodiments, lower plate 1 is attached to six tie rods 7 with six tamper proof flat head cap screws 10. In some embodiments, center support plates 2 and 3 are assembled with the pole clamp 5 to create a deployable mounting mechanism. Pivot pin 4 is pressed fit into center support plate 2, and is passed through pole clamp 5 and is press fit into opposite center support plate 3. Three stop pins 6 are pressed into receiving holes in center support plate 2 and 3. Two stop pins 6 form the stop for the pole clamp 5 deployed position, one stop pin 6 form the stop for the stowed position. Clamp knob 8 has a threaded shaft that is screwed through pole clamp 5. The sub assembly of center support plates 2 and 3, pins 4 and 6, and pole clamp 5 and knob 8 creates the deployable mounting mechanism. The sub assembly is then attached to lower plate 1 with four tamper proof flat head cap screws 10. Herein, item 1 is used for both upper plate and lower plate as the plates are the same part. Face plate 25 is inserted into grooves in the center support plates 2 and 3 and slid towards the lower plate 1 until it contacts the lower plate 1. O ring 9 can be formed from an elastomeric material such as Silicone or Viton. One O ring 9 is added to the top of each cartridge assembly at the upper outlet flange 18. A cartridge assembly with O ring 9 is inserted into each side of the frame housing between tie rods 7 and center support plates 2 and 3. Upper plate 1 is placed on top of the assembly and secured to the tie rods 7 and center support plates 2 and 3 with ten tamper proof flat head cap screws 10. The O rings 9 are captured between upper plate 1 and upper outlet flanges 18 such that the cartridges can smoothly rotate within the housing frame without being loose or creating excessive compression of the cartridge within the housing frame.

Figure 9:
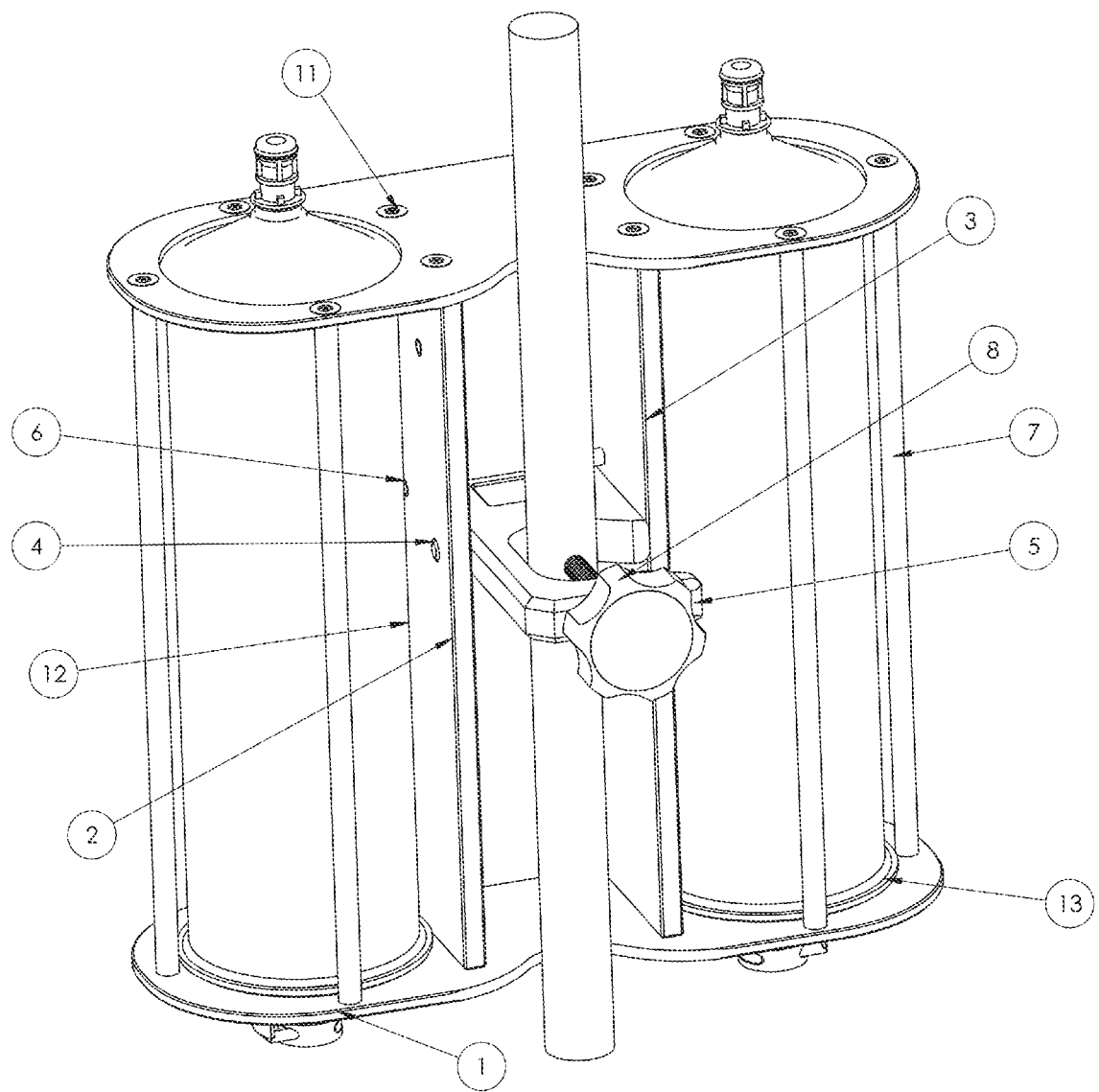
FIG. 9 shows a perspective view from back of dual filter cartridges mounted in a single frame with mounting means deployed and connected to a pole such as an IV pole.

In some embodiments of the invention, the filter system can be packaged, labeled, and sterilized by the manufacturer. It can be shipped to the customer alone or as a component of a comprehensive kit containing all components needed to perform a procedure. Once in use the technician setting up the system will open the packaging while maintaining sterility of inlet connector 15 and outlet connector 19. As shown in FIG. 9, the pole clamp 5 can be deployed from its storage position between center support plates 2 and 3. The pole clamp 5 can rotate around pivot pin 4 and contact stop pins 6, which limits the clamp rotation to a perpendicular orientation. The pole clamp 5 can be placed around an available IV pole or similar available structure in the operating room. The frame is secured to a pole by tightening clamp knob 8 on to the pole.

Figure 10:
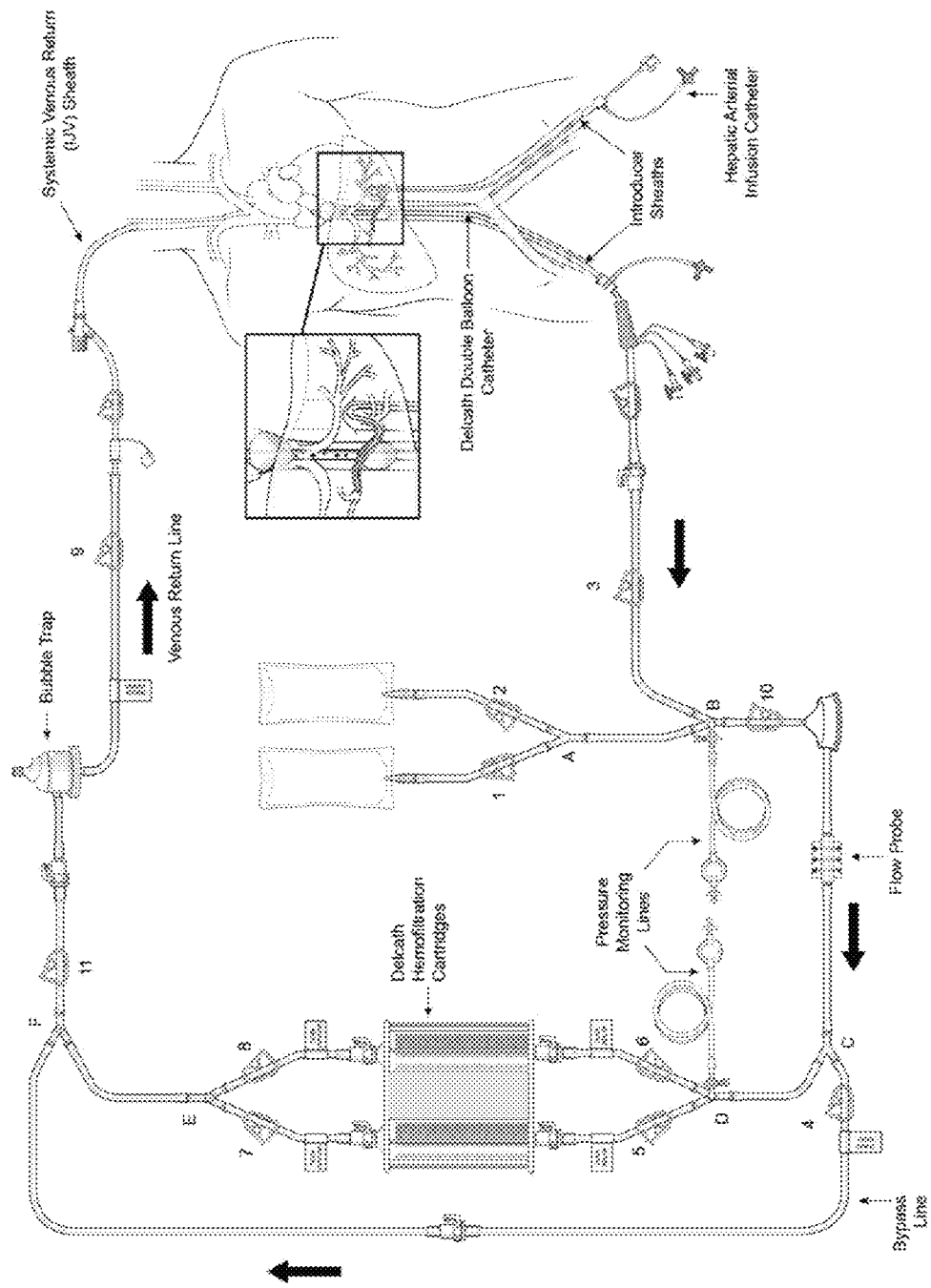
FIG. 10 shows dual filter cartridges mounted in a single frame in an extracorporeal blood filtration set up incorporated into a percutaneous hepatic perfusion procedure.

The technician and physician team can then assemble the system connect tubing between the filter system and other components which make up a complete circuit such as pump, saline supply bags, and flow rate monitor. The tube set which connects to the filter uses rotatable connectors to connect to inlet connectors 15 and outlet connector 19. All components are primed and flushed with saline. The technician will slowly fill the filters with saline from the bottom up allowing air to escape from the top. Due to the high surface area of some filter media, air will often be trapped in the filter cartridge and will need to be coaxed to leave by slowly flushing saline through the filter while tapping the filter cartridge walls to break the air bubbles free. To insure that all air has been removed the technician can rotate the cartridge within the frame to view the entire circumference of the cartridge. Once the filters are primed, the final connections can be made to the isolation aspiration catheter which acts as a supply catheter and the venous return catheter, already placed in location in the patient as shown in FIG. 10. The procedure can then be performed with a secure and safe system.

What is claimed is:

1. A filter apparatus, comprising:
   two or more filter cartridges each having a first end with an inlet and a first screen, a second end with an outlet and a second screen, and walls configured to contain a filter media;
   a housing comprising an upper plate and a lower plate oriented substantially parallel to each other and configured to hold the two or more filter cartridges in about the same orientation, the upper plate and the lower plate each defining two or more openings to which the two or more filter cartridges are rotatably coupled; and
   an attachment clamp connected to the housing,
   wherein the two or more filter cartridges extend through the two or more openings, the upper plate, and the lower plate.

2. The filter apparatus of claim 1, wherein the housing further comprises one or more support elements connecting the upper plate and the lower plate.

3. The filter apparatus of claim 2, wherein the attachment clamp is connected to one or more of the one or more support elements.

4. The filter apparatus of claim 2, wherein the one or more support elements comprise a combination of rods and support plates.

5. The filter apparatus of claim 1, wherein the attachment clamp is a pole clamp.

6. The filter apparatus of claim 1, wherein the walls configured to contain the filter media comprise a cartridge tube.

7. The filter apparatus of claim 6, wherein the cartridge tube is transparent.

8. The filter apparatus of claim 6, wherein the inlet includes an inlet connector and the outlet includes an outlet connector.

9. The filter apparatus of claim 8, wherein the outlet connector is connected to the cartridge tube by an outlet flange.

10. The filter apparatus of claim 9, wherein the outlet flange is conical.

11. The filter apparatus of claim 10, wherein the inlet connector is connected to the cartridge tube by an inlet flange.

12. The filter apparatus of claim 1, wherein the filter media comprises activated carbon.

13. The filter apparatus of claim 12, wherein the filter media is hydrogel coated activated carbon.

14. The filter apparatus of claim 1, wherein the walls configured to contain the filter media define a cylindrical shape.

15. A filter apparatus, comprising:
   two filter cartridges each having a first end with an inlet comprising an inlet connector connected to a cartridge tube by an inlet flange and a first screen and a second end with an outlet comprising an outlet connector and connected to the cartridge by a conical outlet flange and a second screen, and a transparent cartridge tube configured to contain a filter media;

a housing comprising an upper plate and a lower plate oriented substantially parallel to each other and configured to hold the two filter cartridges in about the same orientation, the upper plate and the lower plate each defining two openings to which the two filter cartridges are rotatably coupled;

support elements comprising support plates and rods connecting the upper plate to the lower plate; and a pole clamp connected to the support plates, wherein the two filter cartridges extend through the two openings, the upper plate, and the lower plate.

16. The filter apparatus of claim 15, wherein the filter media comprises activated carbon.

17. The filter apparatus of claim 15, wherein the cartridge tubes are comprised of a transparent material selected from the group consisting of a polysulfone, a polycarbonate, a polypropylene and an acrylic.

18. A housing comprising:

a connected structure comprising an upper plate and a lower plate oriented substantially parallel to each other and configured to hold two or more filter cartridges in about the same orientation, the upper plate and the lower plate each defining two or more openings configured to receive the two or more filter cartridges and configured to rotatably engage the two or more filter cartridges;

one or more support elements connecting the upper plate and the lower plate; and an attachment clamp connected to the housing, wherein the two or more filter cartridges extend through the two or more openings, the upper plate, and the lower plate.

19. The filter apparatus of claim 1, wherein the attachment clamp is rotatably coupled to the housing.

20. The filter apparatus of claim 15, wherein the pole clamp is rotatably coupled to the support plates.

21. The housing of claim 18, wherein the attachment clamp is rotatably coupled to the housing.

* * * * *